United States Patent [19]

Nishida et al.

[11] Patent Number: 5,540,830
[45] Date of Patent: Jul. 30, 1996

[54] METHOD FOR PRODUCING DISILANES

[75] Inventors: Ryoichi Nishida, Ikoma; Shinichi Kawasaki, Tsuzuki-gun; Hiroaki Murase, Kyoto, all of Japan

[73] Assignee: Osaka Gas Company Limited, Osaka, Japan

[21] Appl. No.: 400,581

[22] Filed: Mar. 8, 1995

[30] Foreign Application Priority Data

Mar. 9, 1994 [JP] Japan .................................. 6-038587
Jan. 18, 1995 [JP] Japan .................................. 7-006054

[51] Int. Cl.$^6$ ........................................................ C25B 3/00
[52] U.S. Cl. ................................. 205/414; 205/420
[58] Field of Search .............................. 204/59 R, 59 F

[56] References Cited

U.S. PATENT DOCUMENTS 5,120,406  6/1992  Shono et al. ........................ 204/59 R

FOREIGN PATENT DOCUMENTS

0446578A2  9/1991  European Pat. Off. .
264683    11/1991  Japan .

OTHER PUBLICATIONS

Gilman, et al; Journal of Organometallic Chemistry; 13 (1986) Hexasubstituted Disilanes from Chlorosilanes and Lithium in Tetrahydrofuran; 323–328; (printed in The Netherlands).

Hengge, et al; Journal of Organometallic Chemistry; 212 (1981); An Electro–Chemical Method for the Synthesis of Silicon–Silicon Bonds; 155–161; (printed in The Netherlands).

Shono, et al; J. Chem. Soc., Chem. Commun.; Electroreductive Formation of Polysilanes; 1160–1161.

Japanese Unexamined Patent Publication (Kokai) No. 264, 683/1991 published on Nov. 25, 1991 and a partial translation thereof.

Biran; et al; Inorganic and Organometallic Polymers with Special Properties; (1992) 206; 79–85.

Primary Examiner—John Niebling
Assistant Examiner—Kishor Mayekar
Attorney, Agent, or Firm—Larson and Taylor

[57] ABSTRACT

A method for producing disilane characterized in that halosilane is subjected to electrochemical reaction using Al, Al alloy, Mg, Mg alloy, Cu, Cu alloy, Zn or Zn alloy as anode, lithium salt as supporting electrolyte, Al salt, Fe salt, Mg salt, Zn salt, Sn salt, Co salt, Pd salt, V salt, Cu salt, Ca salt, Na salt or K salt as current carrying aid, and aprotic solvent as solvent, thereby producing disilane.

6 Claims, 4 Drawing Sheets

METHOD FOR PRODUCING DISILANES

TECHNICAL FIELD

The present invention relates to a method for production of disilanes.

PRIOR ART AND ITS PROBLEMS

Disilanes are attracting attention for their use as catalysts in preparing drugs, ceramic precursors, optoelectronic materials, intermediates for producing compounds containing Si—Si bond, etc.

Heretofore, a method for producing disilane is known wherein in the presence of alkali metals such as metallic sodium or alkaline earth metals, halosilane dissolved in a solvent is subjected to reductive coupling with stirring at or around the boiling point of the solvent (J. Organomet. Chem., 13 (1968) 323–328). However, the method has the following drawbacks: It requires to be performed under severe reaction conditions (e.g., heat must be applied for a prolonged time). It inevitably produces a by-product of disiloxane originated from an oxide film on the metal surface. And the use of alkali metal in large amount poses a serious safety problem where disilane is industrially mass-produced.

To overcome these drawbacks, several methods for producing disilane under moderate conditions have been proposed, as described below. Those methods are carried out by subjecting chlorosilane to electrode reduction at room temperature.

Method (1) uses mercury or cadmium as anode, tetra-n-butylammonium perchlorate as supporting electrolyte and 1,2-dimethoxyethane as solvent (J. Organomet. Chem., 212 (1981) 155).

Method (2) uses a metal such as Mg, Al or the like as electrode, lithium perchlorate as supporting electrolyte and tetrahydrofuran (THF) as solvent (J. Chem. Soc., Chem. Commun., 1160, 1990, Japanese Unexamined Patent Publication No. 3-264683).

Method (3) uses Al as electrode, THF plus hexamethylphosphoric triamide (HMPA) as supporting electrolyte and inexpensive lithium chloride as solvent (NATO ASI Ser. Ser. E, 206, 79–85, 1992).

However, the method (1) has drawbacks in that the use of mercury or cadmium as anode poses a serious problem in view of handling, safety and environmental pollution, and the method gives a poor yield of disilane of about 10%.

The method (2) does not pollute the environment, owing to a finding of an efficient electroreductive system employing a safe metal anode. The method has an ease of handling and gives a high yield of about 80–90% of disilane. However, lithium perchlorate used as supporting electrolyte is expensive and must be handled carefully. Hence there remains a need for developing a new system using as supporting electrolyte a compound which is inexpensive and easy to handle.

The method (3) uses lithium chloride as supporting electrolyte that is inexpensive and easy to handle. However, THF is low in solubility of lithium chloride, leading to an extremely poor conductivity of electric current, and the method requires a prolonged application of electricity and the reaction is substantially impossible to complete. In order to accelerate the reaction, the addition of HMPA or the like is essential, which is suspected to be carcinogenic and presents another problem.

PROBLEMS TO BE SOLVED BY THE INVENTION

It is a principal objective of the present invention to provide a new method for producing disilanes, which can be performed with an ease of handling, safety, a low cost and in a high yield.

MEANS FOR SOLVING THE PROBLEMS

The inventors conducted extensive research to resolve the above problems of conventional techniques and discovered that the prior art problems can be substantially obviated or significantly mitigated by using a specific chemical compound which ensures a stable electric current passage (hereinafter referred to as "current carrying aid") in the reaction system during the electroreduction of halosilane for producing disilane by employing a specified metal anode, a specified solvent and a specified supporting electrolyte.

The present invention provides a method for producing disilane as described below:

1. A method for producing disilane characterized in that halosilane of the general formula

(wherein $R_1$, $R_2$ and $R_3$ are the same or different and represent hydrogen atom, alkyl group, aryl group, alkoxy group or amino group, and X represents halogen atom) is subjected to electrochemical reaction using Al, Al alloy, Mg, Mg alloy, Cu, Cu alloy, Zn or Zn alloy as anode, lithium salt as supporting electrolyte, Al salt, Fe salt, Mg salt, Zn salt, Sn salt, Co salt, Pd salt, V salt, Cu salt, Ca salt, Na salt or K salt as current carrying aid, and aprotic solvent as solvent, thereby producing disilane of the general formula

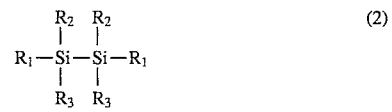

(wherein $R_1$, $R_2$ and $R_3$ are as defined above).

DETAILED DESCRIPTION OF THE INVENTION

Figure 1:
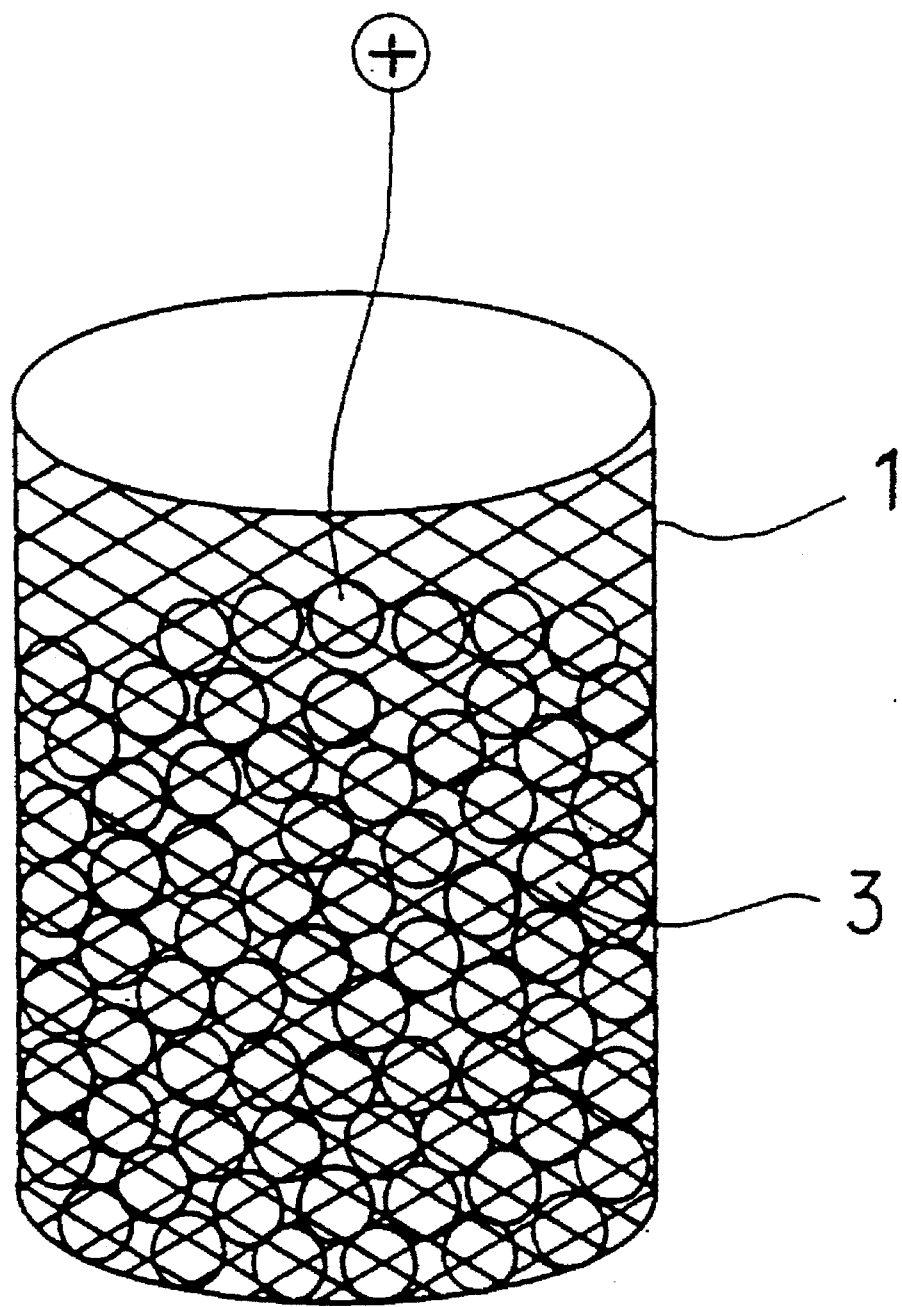
FIG. 1 is an oblique view of a basket-like container or a basket used in the method of the present invention which contains metal or alloy balls constituting anode.

The starting material halosilane used in the present invention is represented by the general formula

 (1)

(wherein $R_1$, $R_2$ and $R_3$ are the same or different and represent hydrogen atom, alkyl group, aryl group, alkoxy group or amino group, and X represents halogen atom).

The reaction product of the present invention is disilane of the general formula

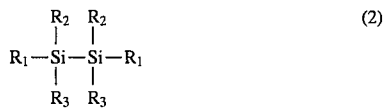 (2)

(wherein $R_1$, $R_2$ and $R_3$ are as defined above).

In the halosilane of the general formula (1), $R_1$, $R_2$ and $R_3$ represent hydrogen atom, amino group and organic substituents (alkyl group, aryl group and alkoxy group). $R_1$, $R_2$ and $R_3$ may be different, or at least two of them may be the same. Examples of the alkyl group are those having 1 to 10 carbon atoms, among which those of 1 to 6 carbon atoms are preferable. Examples of the aryl group include, for example, phenyl group, phenyl group substituted with at least one alkyl group of 1 to 6 carbon atoms, p-alkoxyphenyl group substituted with at least one alkoxy group of 1 to 6 carbon atoms, etc. Examples of the alkoxy group are those having 1 to 10 carbon atoms, among which those of 1 to 6 carbon atoms are preferred. When $R_1$, $R_2$ and $R_3$ are amino group or organic substituents, hydrogen atom or atoms may be substituted with other functional group such as alkyl, aryl or alkoxy group (wherein the number of carbon atoms may be the same as those defined above).

In the halosilane of the general formula (1), X represents halogen atom (Cl, F, Br and I). Cl is more preferable as halogen atom.

In the method of the invention, halosilanes of the general formula (1) are usable singly or at least two of them can be used in mixture. Halosilane of the highest purity is preferably used. As a preliminary treatment for use, liquid halosilane is preferably dried over calcium hydride and then distilled, and solid halosilane is preferably purified by subjecting it to recrystallization.

Prior to initiating the reaction, the halosilane is dissolved in a solvent. Examples of useful solvents include a wide range of aprotic solvents. Specific examples of useful aprotic solvents are propylene carbonate, acetonitrile, dimethylformamide, dimethylsulfoxide, 1,2-dimethoxyethane, bis(2-methoxyethyl)ether, p-dioxane, tetrahydrofuran, methylene chloride, etc. These solvents are usable singly or at least two of them can be used in mixture. Among the solvents, ether solvents are more preferable, and most preferable are tetrahydrofuran and 1,2-dimethoxyethane. Too low a concentration of halosilane in the solvent causes reduction of the current efficiency. Contrarily, too high a concentration thereof may deteriorate the solubility of supporting electrolyte. A suitable concentration of the halosilane in the solvent is about 0.05 to about 6 mols/l, preferably about 0.1 to about 4 mols/l, more preferably about 0.3 to about 3 mols/l.

Examples of supporting electrolytes usable in the invention are such inexpensive lithium salts as LiCl, LiNO$_3$, Li$_2$CO$_3$, etc. These supporting electrolytes are usable singly or at least two of them can be used in mixture. Among the supporting electrolytes indicated above, LiCl is most preferable. Too low a concentration of the supporting electrolyte in the solvent fails to proceed a satisfactory reaction even if the current carrying aid described below is included in the reaction system. Hence it is used at a concentration over 0.01 mol/l. A suitable concentration of the supporting electrolyte in the solvent is preferably about 0.05 to about 1.1 mols/l, most preferably about 0.2 to about 1.0 mol/l.

In the present invention, essential is the use of current carrying aid which ensures a satisfactory current passage to run the electrode reaction efficiently, thereby producing a high yield of disilane. As the current carrying aids, preferred are Al salts such as AlCl$_3$, Al(OEt)$_3$, etc.; Fe salts such as FeCl$_2$, FeCl$_3$, etc.; Mg salts such as MgCl$_2$, etc.; Zn salts such as ZnCl$_2$, etc.; Sn salts such as SnCl$_2$, etc.; Co salts such as COCl$_2$, etc.; Pd salts such as PdCl$_2$, etc.; V salts such as VCl$_3$, etc.; Cu salts such as CuCl$_2$, etc.; Ca salts such as CaCl$_2$, etc. These current carrying aids are usable singly or at least two of them can be used in mixture. Among the current carrying aids given above, preferred are AlCl$_3$, FeCl$_2$, FeCl$_3$ CoCl$_2$, CuCl$_2$, etc. Too low a concentration of the current carrying aid fails to ensure a satisfactory current passage. Contrarily, at too high a concentration, the aid itself is reduced and fails to participate in the reaction. A suitable concentration of the current carrying aid in the solvent is about 0.01 to about 2 mols/l, more preferably about 0.01 to about 0.6 mols/l, most preferably about 0.02 to about 0.3 mols/l.

In the present invention, usable as anode are any of Al, alloys principally containing Al, Mg, alloys principally containing Mg, Cu, alloys principally containing Cu, Zn and alloys principally containing Zn. The alloys are not limited insofar they contain one of the above metals as component. For example, alloys containing Al as the main component may contain about 3 to about 10% of Mg, while alloys containing Mg as the main component may contain about 3 to about 10% of Al. Anticorrosive Al alloys, Mg alloys and Zn alloys can also be used. The Japanese Industrial Standards H6125-1961 specifies anticorrosive Mg alloys, among which 1st species (MgAl), 2nd species (MGA2) generally called "AZ63", 3rd species (MGA3) and so on can be used. Preferred anode materials are Al, Al alloys, Mg and Mg alloys. Cathode materials are not limited insofar as the electric current can flow. Examples of the cathode materials are stainless steels such as SUS 304, SUS 316, etc.; metals such as Mg, Cu, Zn, Al, Ni, Co, etc.; and carbon materials. The electrode shape is not limited insofar as the electric current can stably flow. Preferred examples of the electrode shape are bar, plate, tube, cone, disc, coiled plate, etc. The electrode in the form of metal or alloy balls contained in a basket is also preferred. If desired, oxide film is removed from the electrode surface prior to initiating the reaction. The removal of oxide film from the electrode can be performed by any method, as by washing the electrode with an acid and subsequently washing with ethanol and ether and then drying it under reduced pressure, by polishing the electrode in a nitrogen atmosphere, or by conducting a combination of the above methods, etc.

The present invention can be carried out in various manners, among which the following two processes are preferable: Process (a) comprising charging the halosilane of the general formula (1), the supporting electrolyte, the current carrying aid and the solvent into a static electrolytic cell with an anode and a cathode placed therein; subsequently applying a specific amount of electricity, preferably with stirring by mechanical or magnetic means; and thereby running the electrochemical reaction. Process (b), which are performed in a flow-type electrolytic cell system composed of an electrolytic cell with an anode and a cathode installed therein, an electrolyte tank, a pump, a pipe and so on, comprising charging the reaction solution consisting of the halosilane, the supporting electrolyte, the current carrying aid and the solvent into the electrolyte tank; circulating the solution by pumping across the electrolytic cell system; subsequently applying a specific amount of electricity; and thereby undergoing the electrochemical reaction.

Figure 2:
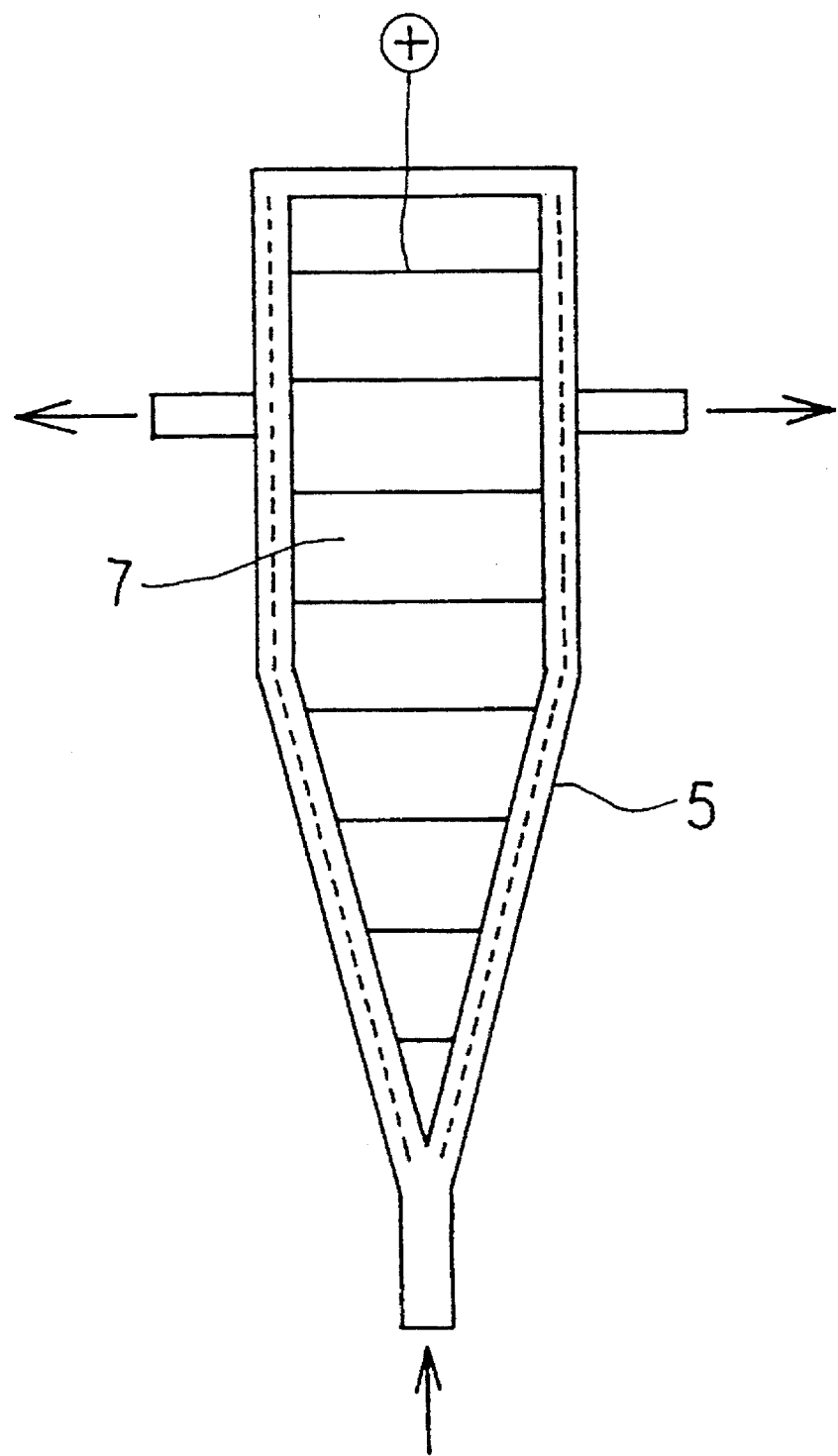
FIG. 2 is a cross sectional view illustrating an electrolytic cell which takes the shape of pencil sharpener usable in the method of the present invention.

The structure and shape of the electrolytic cell are not limited, but a preferred example is a structure which enables to supply easily the anode-constituting material which dissolves from the electrode into the electrolyte and is gradually consumed as the reaction progresses. As shown in FIG. 1, the cell may have as an anode a basket or basket-form container containing small balls or pellets which can be supplied easily. As outlined in FIG. 2, usable also is a structure of the electrolytic cell designed to contain a layer of anode blocks 7 within a cathode sheet 5, pursuant to the example of "pencil sharpener form electrolytic bath" disclosed in the Japanese Unexamined Patent Publication No. 62-56589. Such electrolytic cells, devised to continuously supply anode elements, can dispense with exchange procedure of consumable electrodes per a reaction cycle or per several reaction cycles and therefore allows repeating reaction cycles for a long period of time. Thus the method lowers the expenses needed for exchanging anode, thereby reducing the cost for producing disilanes.

The reactor or the reaction system preferably has a dry atmosphere, more preferably an atmosphere of dry nitrogen or inert gas, even more preferably a deoxidized atmosphere consisting of dry nitrogen or inert gas. A current is applied usually in an amount of about 1 to about 10 F/mol, more preferably about 1 to about 6 F/mol, most preferably about 1.3 to about 3 F/mol based on halosilane. The reaction period varies depending on the amount of halosilane used as starting material and the resistance of electrolytic solution in association with the amount of supporting electrolyte and current carrying aid. Usually, the reaction period is within a range of about 0.5 to about 100 hours. In case that the starting material halosilane is used at a concentration of 0.67 mols/l, the period is usually about 3 to about 10 hours. The reaction temperature is preferably in the range from −20° C. to the boiling point of the solvent used, more preferably from −5° to 30° C., most preferably from 0° to 25° C.

The present invention may use or can dispense with a diaphragm, which is an essential element in the conventional electrode reduction reaction system.

EFFECTS OF THE INVENTION

The present invention achieves remarkably improved effects as described below.

(a) The present invention gives a high yield of disilanes.

(b) The present invention provides disilanes safely without causing environmental pollution since there is no need for using dangerous metals or carcinogenic solvents.

(c) The present invention produces disilanes with a low cost since inexpensive supporting electrolytes are used.

(d) The present invention produces disilanes efficiently within a shortened reaction period since good current passage is ensured during the reaction.

EXAMPLES

The following examples are intended to illustrate the present invention in further detail.

Example 1

0.40 g of anhydrous lithium chloride (LiCl) and 0.25 g of anhydrous aluminum chloride ($AlCl_3$) were fed to a 30 ml—volume three-necked flask (hereinafter referred to as "reactor") equipped with a three-way cock, an Al anode (1 cm in diameter×5 cm in length) and a SUS 304 cathode (1 cm×1 cm×5 cm). The reactor was heated to 50° C. under reduced pressure of 1 mmHg, thereby drying LiCl and $AlCl_3$. Oxygen free and dry nitrogen was charged into the reactor. Then 15 ml of tetrahydrofuran preliminarily dried over sodium-benzophenone ketyl was added. 1.3 ml (10 mmol) of trimethylchlorosilane preliminarily purified by distillation was added with a syringe. While the reaction solution was stirred with a magnetic stirrer and the reactor was maintained at room temperature using a water bath, an electric current was applied from a constant-voltage source. The current was applied for about 3.5 hours to pass 2 F/mol of electricity based on the trimethylchlorosilane.

After completion of the reaction, 20 ml of hexane was added to the reaction solution for salting-out and then the hexane layer was subjected to fractional distillation, thereby giving a product.

Analysis of the product revealed that hexamethyldisilane was produced in a yield of 91.3% and the result confirmed that disilane can be produced in a high yield according to the present invention.

Disiloxane contained as a by-product was in a proportion not more than 0.1%.

Example 2

An electrochemical reaction was conducted in the same manner as in Example 1 with the exception that as the starting material of the general formula (1) 1.65 ml (10 mmol) of dimethylphenylchlorosilane purified by distillation was used. The product obtained was 1,2-diphenyl-1,1,2,2-tetramethyldisilane in a yield of 93.9% and the result confirmed that disilane was produced in a high yield.

Example 3

An electrochemical reaction was conducted in the same manner as in Example 1 with the exception that as the starting material of the general formula (1) 2.06 ml (10 mmol) of methyldiphenylchlorosilane purified by distillation was used. The product obtained was 1,2-dimethyl-1,1,2,2-tetraphenyldisilane in a yield of 88.5% and the result confirmed that disilane can be produced in a high yield.

Example 4

An electrochemical reaction was conducted in the same manner as in Example 1 with the exception that as the starting material of the general formula (1) 1.48 g (5 mmol) of triphenylchlorosilane purified by recrystallization was used. Hexaphenyldisilane was obtained in a yield of 92.7% and the result confirmed that disilane was produced in a high yield.

Example 5

An electrochemical reaction was conducted in the same manner as in Example 1 with the exception that 1.31 ml (10 mmol) of trimethylbromosilane was used as the starting material of the general formula (1). Hexamethyldisilane was produced in a yield of 82.3% and the result confirmed that disilane can be produced in a high yield according to the invention.

Example 6

Trimethylchlorosilane was subjected to electrochemical reaction in the same manner as in Example 1 with the exception that Al—Mg alloy (Al 90%, Mg 10%, 1 cm×1 cm×5 cm) was used as the anode material. Hexamethyldisilane was obtained in a yield of 90.3% and the result confirmed that disilane was produced in a high yield.

Example 7

Trimethylchlorosilane was subjected to electrochemical reaction in the same manner as in Example 1 with the exception that Mg (1 cm in diameter×5 cm in length) was used as the anode. Hexamethyldisilane was obtained in a yield of 78.3% and the result confirmed that disilane was produced in a high yield.

Example 8

Trimethylchlorosilane was subjected to electrochemical reaction in the same manner as in Example 1 with the exception that Mg alloy (Mg 90.5%, Al 3%, Mn 0.5%, 1 cm×1 cm×5 cm) was used as the anode. Hexamethyldisilane was produced in a yield of 83.3% and the result confirmed that disilane can be obtained in a high yield according to the invention.

Example 9

Trimethylchlorosilane was subjected to electrochemical reaction in the same manner as in Example 1 with the exception that Zn (1 cm×1 cm×5 cm) was used as the anode. Hexamethyldisilane was formed in a high yield.

Example 10

Trimethylchlorosilane was subjected to electrochemical reaction in the same manner as in Example 1 with the exception that glassy carbon (1 cm×0.1 cm×5 cm) was used as the cathode material. Hexamethyldisilane was obtained in a yield of 92.3% and the result confirmed that the invention can produce disilane in a high yield.

Example 11

Trimethylchlorosilane was subjected to electrochemical reaction in the same manner as in Example 1 with the exception that 0.65 g of $LiNO_3$ was used as the supporting electrolyte. Hexamethyldisilane was produced in a high yield.

Example 12

Trimethylchlorosilane was subjected to electrochemical reaction in the same manner as in Example 1 with the exception that 0.70 g of $Li_2CO_3$ was used as the supporting electrolyte. Hexamethyldisilane was obtained in a high yield.

Example 13

Trimethylchlorosilane was subjected to electrochemical reaction in the same manner as in Example 1 with the exception that 0.18 g of $MgCl_2$ was used as the current carrying aid. Hexamethyldisilane was formed in a high yield.

Example 14

Trimethylchlorosilane was subjected to electrochemical reaction in the same manner as in Example 1 with the exception that 0.25 g of $ZnCl_2$ was used as the current carrying aid. Hexamethyldisilane was obtained in a high yield.

Example 15

Trimethylchlorosilane was subjected to electrochemical reaction in the same manner as in Example 1 with the exception that 0.21 g of $CaCl_2$ was used as the current carrying aid. Hexamethyldisilane was formed in a high yield.

Example 16

Trimethylchlorosilane was subjected to electrochemical reaction in the same manner as in Example 1 with the exception that as the solvent 15 ml of 1,2-dimethoxyethane preliminarily dried over sodiumbenzophenone ketyl was used. Hexamethyldisilane was produced in a yield of 90.5% and the result confirmed that Si—Si bonds were formed in a high yield.

Example 17

40 g of anhydrous lithium chloride (LiCl) and 25 g of anhydrous aluminum chloride ($AlCl_3$) were fed to the electrolyte tank of the flow-type electrolytic cell system. The system was composed of a filterpress-type electrolytic cell (distance between the electrodes: 1 cm) equipped with an Al anode (12 cm×15 cm×1 cm) and a cathode made of SUS 316 (12 cm×15 cm×1 cm), a 3 ——volume electrolyte tank, a bellows-type pump and circulation pipes. Deoxidized dry nitrogen was introduced into the electrolytic cell system. Then 1.5 l of tetrahydrofuran preliminarily dried over sodiumbenzophenone ketyl was added. 130 ml (1 mol) of trimethylchlorosilane preliminarily purified by distillation was added. While circulating the electrolyte by means of the bellows-type pump (linear velocity between the electrodes: 10 cm/sec.) and maintaining the reaction temperature at room temperature by means of a cooler, an electric current was applied from a constant-voltage source. The current was applied for about 3.5 hours to pass 2 F/mol of electricity based on the trimethylchlorosilane.

After completion of the reaction, 2 l of hexane was added to the electrolyte for salting-out and then the hexane layer was subjected to fractional distillation to give a product.

Analysis of the product revealed that hexamethyldisilane was produced in a yield of 93.6% and the result confirmed that disilane was produced in a high yield according to the present invention.

Example 18

Trimethylchlorosilane was subjected to electrochemical reaction in the same manner as in Example 1 with the exception that an anticorrosive Mg alloy (2nd species, specified in the Japanese Industrial Standards H6125-1961, [MGA2, generally called "AZ63"]; 1 cm×1 cm×5 cm) was used as the anode. Hexamethyldisilane was obtained in a yield of 84.9% and the result confirmed that disilane was produced in a high yield.

Example 19

Dimethylphenylchlorosilane was subjected to electrochemical reaction in the same manner as in Example 2 with the exception that 0.24 g of $FeCl_2$ was used as the current carrying aid. It took about 3.3 hours for the passed electricity to reach 2 F/mol based on the starting material. 1,2-diphenyl-1,1,2,2-tetramethyldisilane was obtained in a yield of 96.8% and the result confirmed that disilane was produced in a high yield.

Example 20

Trimethylchlorosilane was subjected to electrochemical reaction in the same manner as in Example 1 with the exception that 0.31 g of $FeCl_3$ was used as the current carrying aid. It took about 3.6 hours for the passed electricity to reach 2 F/mol based on the starting material. Hexamethyldisilane was produced in a yield of 91.7% and the result confirmed that disilane was produced in a high yield.

Example 21

Trimethylchlorosilane was subjected to electrochemical reaction in the same manner as in Example 1 with the exception that 0.49 g of $SnCl_2$ was used as the current carrying aid. It took about 4.9 hours for the passed electricity to reach 2 F/mol based on the starting material. Hexamethyldisilane was formed in a yield of 71.3% and the result confirmed that disilane can be produced in a high yield according to the invention.

Example 22

Trimethylchlorosilane was subjected to electrochemical reaction in the same manner as in Example 1 with the exception that 0.24 g of $CoCl_2$ was used as the current carrying aid. It took about 3.9 hours for the passed electricity to reach 2 F/mol based on the starting material. Hexamethyldisilane was formed in a yield of 89.1% and the result confirmed that disilane was produced in a high yield.

Example 23

Trimethylchlorosilane was subjected to electrochemical reaction in the same manner as in Example 1 with the exception that 0.33 g of $PdCl_2$ was used as the current carrying aid. It took about 3.2 hours for the passed electricity to reach 2 F/mol based on the starting material. The reaction afforded hexamethyldisilane in a yield of 90.1% confirming that disilane can be produced in a high yield according to the invention.

Example 24

Trimethylchlorosilane was subjected to electrochemical reaction in the same manner as in Example 1 with the exception that 0.29 g of $VCl_3$ was used as the current carrying aid. It took about 5.2 hours for the passed electricity to reach 2 F/mol based on the starting material. Hexamethyldisilane was obtained in a yield of 65.2% and the result confirmed that disilane was produced in a high yield.

Example 25

Trimethylchlorosilane was subjected to electrochemical reaction in the same manner as in Example 1 with the exception that 0.25 g of $CuCl_2$ was used as the current carrying aid. It took about 3.3 hours for the passed electricity to reach 2 F/mol based on the starting material. Hexamethyldisilane was produced in a yield of 70.9% and the result confirmed that disilane was produced in a high yield.

Example 26

Figure 3:
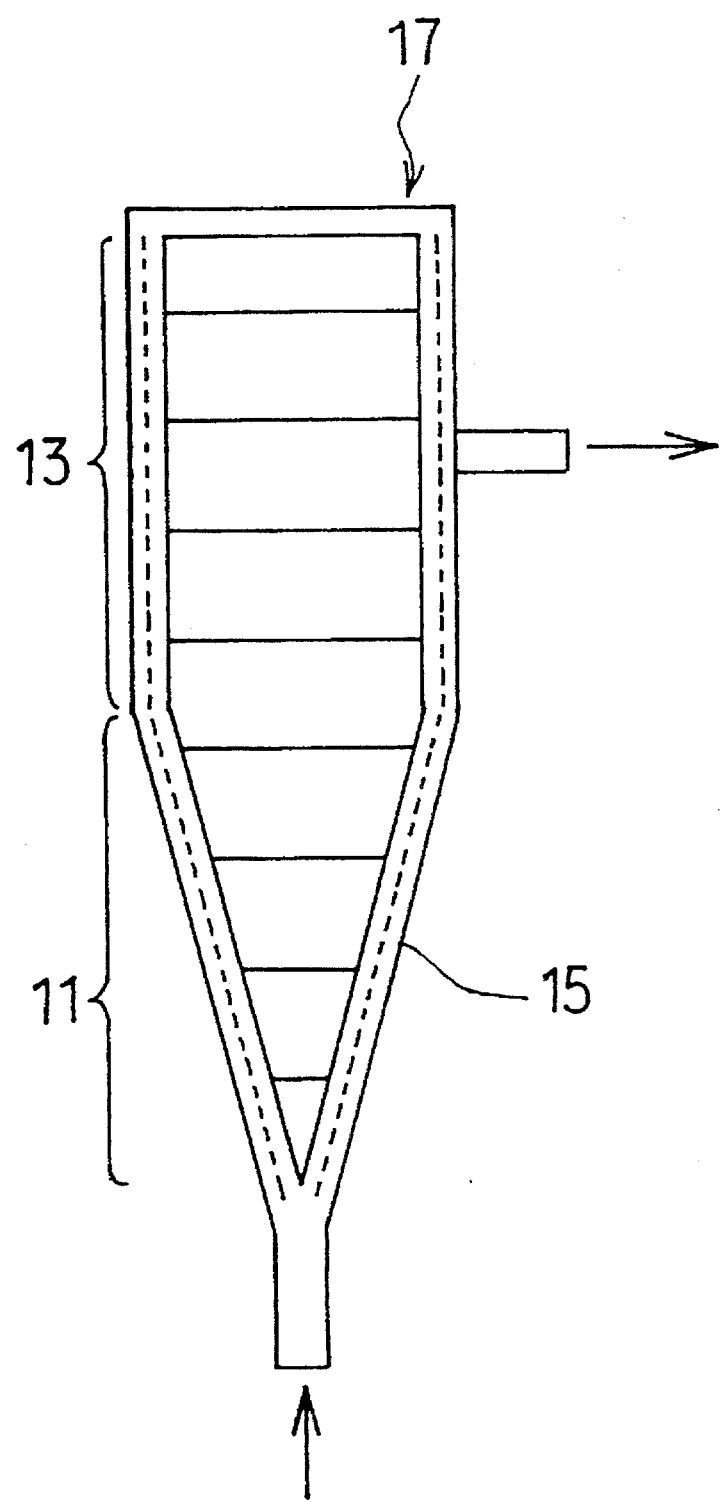
FIG. 3 is a cross sectional view schematically showing an electrolytic cell in the shape of a pencil sharpener used in the Examples of the present invention.

The method of the present invention was carried out using the pencil sharpener form electrolytic cell as illustrated in FIG. 3. A pencil sharpener form electrolytic cell 17 containing an anode of built-up bodies made of aluminum composed of cone 11 (105 cm in height×22 cm in diameter) and cylinder 13 (22 cm in diameter×45 cm in thickness, composed of three blocks each 15 cm in thickness) and a cathode sheet 15 made of SUS 304 (the sheet partly constituted the external wall of the electrolytic cell) placed at 5 mm distance from the anode cone 11; a 20 l—volume electrolyte tank (which is not illustrated in the drawing); circulation pipes (which are not illustrated in the drawing) and so on were equipped as primary components in the flow-type electrolytic cell system. 400 g of anhydrous lithium chloride (LiCl) and 250 g of anhydrous ferrous chloride ($FeCl_2$) were fed into the cell and then deoxidized dry nitrogen was introduced. Then 15 l of dried tetrahydrofuran was added. Into the mixture, 0.85 kg of trimethylchlorosilane was added. While circulating the electrolyte by means of a circulation pump (linear velocity at the intermediate point between the electrodes: 20 cm/sec.) and maintaining the reaction temperature at room temperature by means of a cooler, constant-current electrolysis was conducted at a current value of 34 A. The current was applied for about 12.3 hours to pass 2 F/mol of electricity based on the trimethylchlorosilane.

After completion of the reaction, the electrolyte was washed, extracted and reprecipitated in accordance with the conventional method to yield 486 g of hexamethyldisilane.

Observation of the Al electrode consumption after the reaction indicated that the Al electrode was consumed and shortened by about 1.4 mm at the upper end. In view of the extent of the consumption, it is apparent that the upper portion of the cylinder 13 constituting Al anode, 45 cm in height (three blocks each 15 cm in height) will be consumed completely and there will be a need to supply another Al block only after the above reaction cycle is repeated about 320 times.

Example 27

Figure 4:
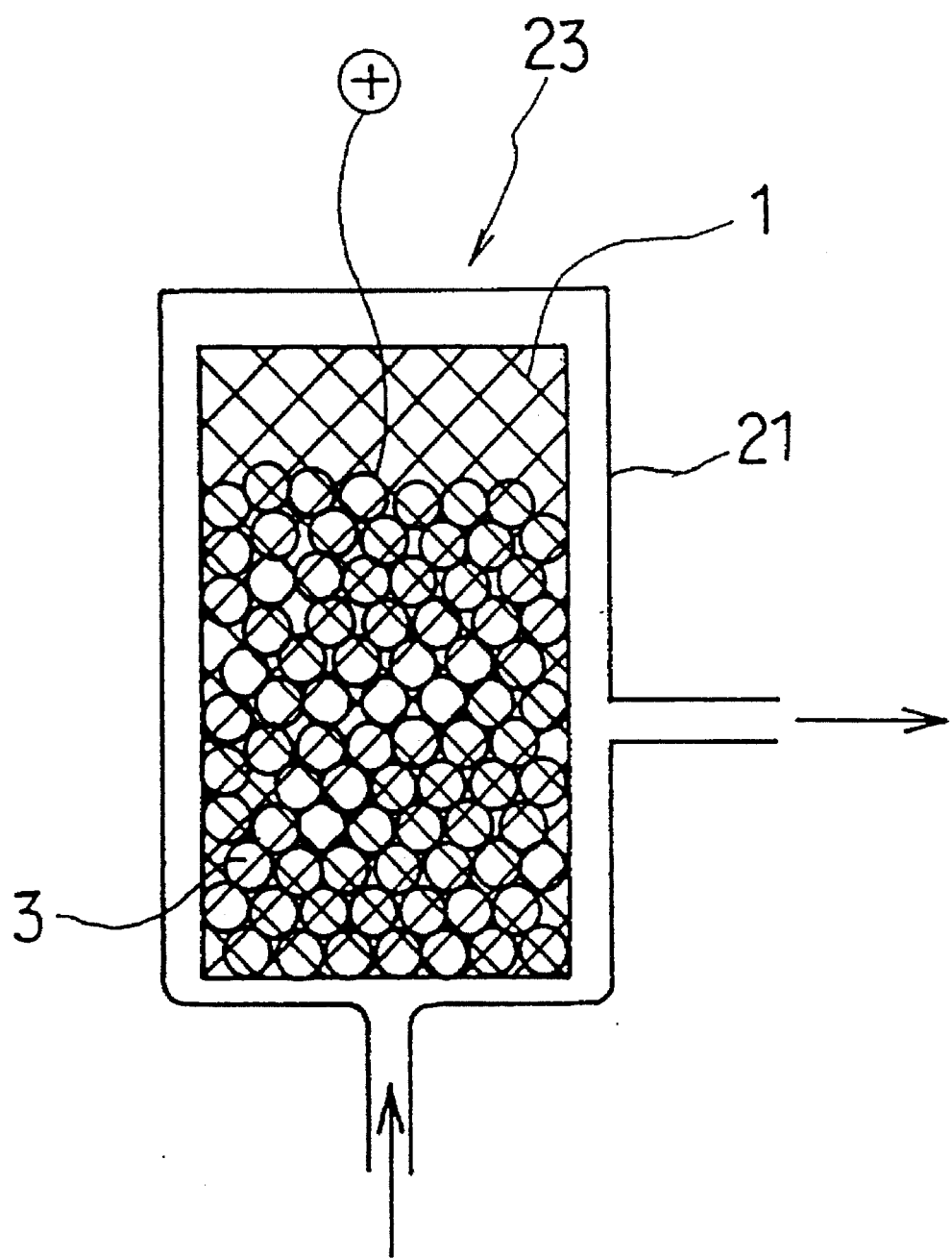
FIG. 4 is a cross sectional view schematically showing an electrolytic cell employing aluminum balls placed in a basket as consumable electrode.

The method of the invention was performed using an anode of the type illustrated in FIG. 1 and an electrolytic cell of the type illustrated in FIG. 4. The electrolytic cell 23 containing as the anode Al balls 3 (diameter 1 cm) placed in a basket 1 made of PTFE (20 cm in diameter×40 cm in height) up to 35 cm high from the bottom of the basket and a cathode of cylinder-type container 21 made of SUS 304, placed at 5 mm distant from the basket 1; a 20 l—volume of electrolyte tank (which is not illustrated in the drawing); circulation pipes (which are not illustrated in the drawing) and so on were equipped as primary components in the flow-type electrolytic cell system. 400 g of anhydrous lithium chloride (LiCl) and 250 g of anhydrous ferrous chloride ($FeCl_2$) were fed. Deoxidized dry nitrogen was introduced into the reaction device. Then 15 l of dried tetrahydrofuran was added. Into the mixture, 0.85 kg of trimethylchlorosilane was added. While circulating the electrolyte by means of a circulation pump (linear velocity between the electrodes: 20 cm/sec.) and maintaining the reaction temperature at room temperature by means of a cooler, constant-current electrolysis was conducted at a current value of 34 A. The current was applied for about 12.3 hours to pass 2 F/mol of electricity based on the trimethylchlorosilane.

After completion of the reaction, the electrolyte was washed, extracted and reprecipitated in accordance with the conventional method to yield 453 g of hexamethyldisilane.

Observation of the Al electrode consumption after the reaction indicated that the Al electrode was consumed and shortened by about 0.3 cm at the upper end. In view of the extent of the consumption, it is apparent that the height of Al balls was lowered from the upper end by one third and thus there is no need to supply another Al ball until the above reaction is repeated about 70 times.

We claim:

1. A method for producing disilane comprising the steps of subjecting a halosilane of the general formula

wherein $R_1$, $R_2$ and $R_3$ are the same or different and represent hydrogen atom, alkyl group, aryl group, alkoxy group or amino group, and X represents halogen atom to an electrochemical reaction using Al, Al alloy, Mg, Mg alloy, Cu, Cu alloy, Zn or Zn alloy as anode, lithium salt as supporting electrolyte, Al salt, Fe salt, Mg salt, Zn salt, Sn salt, Co salt, Pd salt, V salt, Cu salt or Ca salt as current carrying aid, and aprotic solvent as solvent, to produce a disilane of the general formula

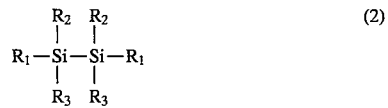

wherein $R_1$, $R_2$ and $R_3$ are as defined above.

2. A method according to claim 1 wherein Al, Al alloy, Mg or Mg alloy are used as the anode.

3. A method according to claim 1 wherein LiCl is used as the supporting electrolyte.

4. A method according to claim 1 wherein $AlCl_3$, $FeCl_2$, $FeCl_3$, $CoCl_2$ or $CuCl_2$ are used as the current carrying aid.

5. A method according to claim 1 wherein the halosilane subjected to the electrochemical reaction is trimethylchlorosilane.

6. A method according to claim 5 wherein the product disilane is hexamethyldisilane.

* * * * *